(12) United States Patent
Shiran et al.

(10) Patent No.: US 11,903,898 B2
(45) Date of Patent: Feb. 20, 2024

(54) ULTRASOUND IMAGING WITH REAL-TIME VISUAL FEEDBACK FOR CARDIOPULMONARY RESUSCITATION (CPR) COMPRESSIONS

(71) Applicant: GE Precision Healthcare LLC, Wauwatosa, WI (US)

(72) Inventors: Carmit Shiran, Haifa (IL); Alex Sokulin, Haifa (IL); Dani Pinkovich, Haifa (IL); Cynthia A. Owen, Powhatan, AR (US); Menachem Halmann, Wauwatosa, WI (US); Antonio Fabian Fermoso, Madrid (ES); Mor Vardi, Haifa (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 940 days.

(21) Appl. No.: 16/574,997

(22) Filed: Sep. 18, 2019

(65) Prior Publication Data

US 2021/0077344 A1    Mar. 18, 2021

(51) Int. Cl.
*A61H 31/00* (2006.01)
*G06T 7/00* (2017.01)
(Continued)

(52) U.S. Cl.
CPC ........... *A61H 31/005* (2013.01); *A61B 8/085* (2013.01); *A61B 8/0883* (2013.01); *A61B 8/14* (2013.01);
(Continued)

(58) Field of Classification Search
CPC ......... A61B 8/46; A61B 8/0883; A61B 8/085; A61B 8/5207–5223; G06T 2207/30048;
(Continued)

(56) References Cited

U.S. PATENT DOCUMENTS

| 2016/0143804 | A1* | 5/2016 | Nilsson | A61H 31/006 |
| | | | | 601/41 |
| 2016/0199148 | A1 | 7/2016 | Maracaja-Neto | |
| 2019/0029919 | A1* | 1/2019 | Suh | A61H 31/006 |

OTHER PUBLICATIONS

"Evaluation of Out-of-Hospital Cardiac Arrest Using Transesophageal Echocardiography in the Emergency Department", Felipe Teran et al, Resuscitation 137 (2019), pp. 140-147.
(Continued)

*Primary Examiner* — Boniface Ngathi
(74) *Attorney, Agent, or Firm* — McAndrews, Held & Malloy, Ltd.; Daniel Bissing

(57) ABSTRACT

Systems and methods are provided for ultrasound imaging with real-time feedback for cardiopulmonary resuscitation (CPR) compressions. Ultrasound images generated based on received echo ultrasound signals during cardiopulmonary resuscitation (CPR) of a patient may be processed, and based on the processing of the ultrasound images, real-time information relating to the cardiopulmonary resuscitation (CPR) may be determined. Feedback for assisting in conducting the cardiopulmonary resuscitation (CPR) may be generated based on the information. The feedback may include information and/or indications relating to compressions applied during the cardiopulmonary resuscitation (CPR). The feedback may be configured for outputting during displaying of the generated ultrasound images.

20 Claims, 6 Drawing Sheets

(51) Int. Cl.
  *A61B 8/00*    (2006.01)
  *A61B 8/08*    (2006.01)
  *A61B 8/14*    (2006.01)
  *G06T 7/174*   (2017.01)
  *G06T 7/11*    (2017.01)

(52) U.S. Cl.
  CPC .............. *A61B 8/46* (2013.01); *A61B 8/5223* (2013.01); *A61H 31/007* (2013.01); *G06T 7/0012* (2013.01); *G06T 7/11* (2017.01); *G06T 7/174* (2017.01); *A61B 8/4427* (2013.01); *A61B 8/467* (2013.01); *A61H 2201/5058* (2013.01); *G06T 2207/10132* (2013.01); *G06T 2207/30048* (2013.01); *G06T 2207/30101* (2013.01)

(58) Field of Classification Search
  CPC .......... G06T 7/11; G06T 2207/10132–10136; A61H 31/005; A61H 31/004–007
  See application file for complete search history.

(56) References Cited

OTHER PUBLICATIONS

"The Use of Transesophageal Echocardiography During Cardiac Arrest", Resuscitation, Brian K. Parker, et al., J Ultrasound Med 2019, 38:1141-1151.
CN patent application 202010817152.6 filed Aug. 14, 2020—Office Action dated Oct. 8, 2022; 10 pages.

\* cited by examiner

400

420

ULTRASOUND IMAGING WITH REAL-TIME VISUAL FEEDBACK FOR CARDIOPULMONARY RESUSCITATION (CPR) COMPRESSIONS

FIELD

Aspects of the present disclosure relate to medical imaging. More specifically, certain embodiments relate to methods and systems for ultrasound imaging with real-time feedback for cardiopulmonary resuscitation (CPR) compressions.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Various issues may exist with conventional approaches for utilizing medical imaging. In this regard, conventional systems and methods, if any existed, for utilizing medical imaging during cardiopulmonary resuscitation (CPR), can be inefficient and/or ineffective.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for a ultrasound imaging with real-time feedback for cardiopulmonary resuscitation (CPR) compressions, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
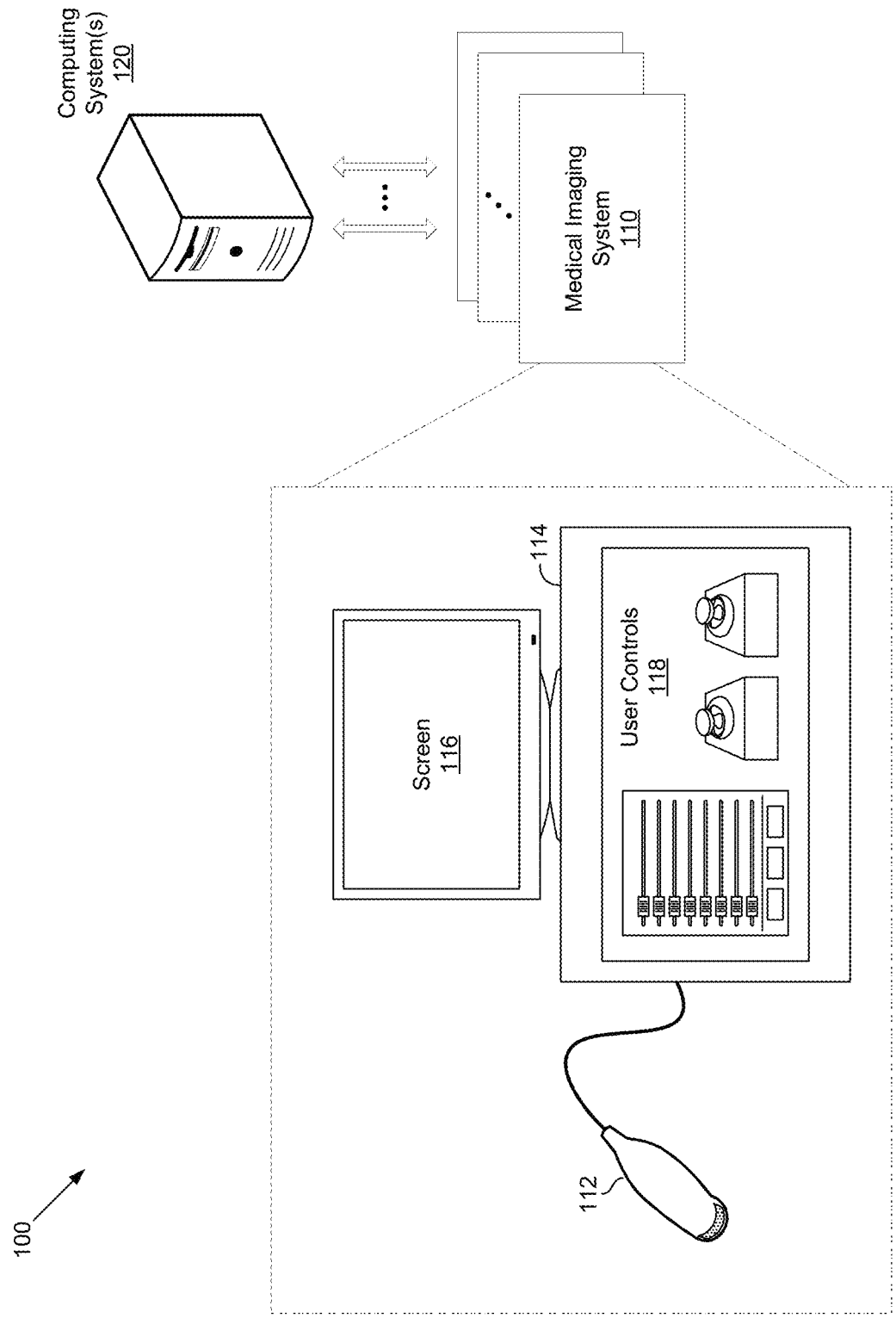
FIG. 1 is a block diagram illustrating an example medical imaging arrangement that supports ultrasound imaging with real-time feedback for cardiopulmonary resuscitation (CPR) compressions, in accordance with the present disclosure.

Certain implementations in accordance with the present disclosure may be directed to ultrasound imaging with real-time feedback for cardiopulmonary resuscitation (CPR) compressions. In particular, various embodiments have the technical effect of enhancing cardiopulmonary resuscitation (CPR), by allowing for providing real-time feedback relating to cardiopulmonary resuscitation (CPR), particularly CPR compressions. This may be done, for example, by processing ultrasound images (or datasets corresponding thereto) to identify structures pertinent to CPR compressions, tracking locations of compression, determining when the compressions (or majority thereof) are applied at correct position, and providing real-time feedback to users based on tracking of CPR compressions, particularly visually within displayed ultrasound images.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIGS. 1 and 2.

Figure 2:
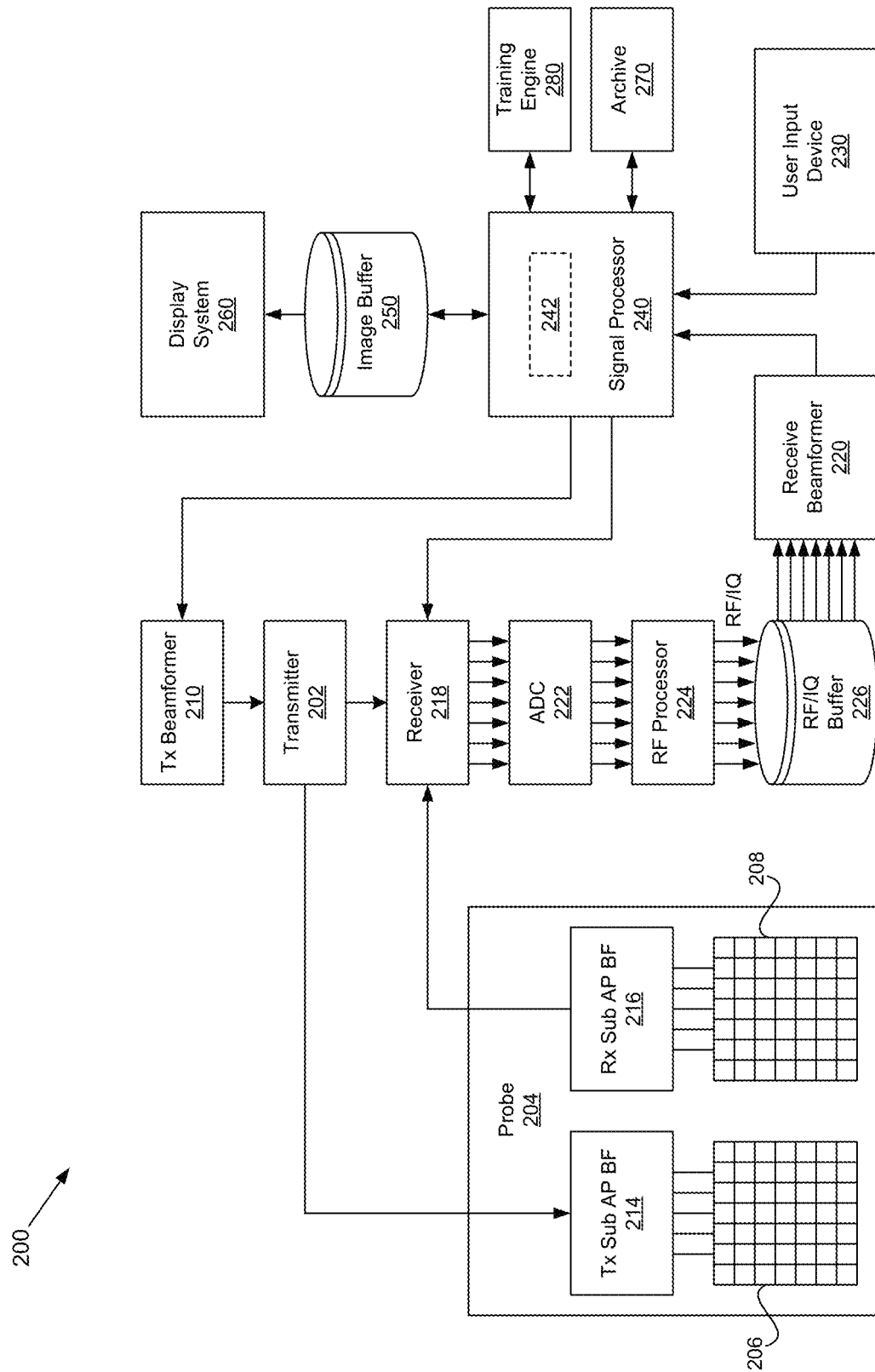
FIG. 2 is a block diagram illustrating an example ultrasound system that supports ultrasound imaging with real-time feedback for cardiopulmonary resuscitation (CPR) compressions, in accordance with the present disclosure.

FIG. 1 is a block diagram illustrating an example medical imaging arrangement that supports ultrasound imaging with real-time feedback for cardiopulmonary resuscitation (CPR) compressions, in accordance with the present disclosure. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 110 may be an ultrasound system, configured for generating and/or rendering ultrasound images. An example implementation of an ultrasound system, which may correspond to the medical imaging system 110, is described in more detail with respect to FIG. 2.

As shown in FIG. 1, the medical imaging system 110 may comprise a probe 112, which may be portable and movable, and a display/control unit 114. The probe 112 may be configured for generating and/or capturing particular type of signals (or data corresponding thereto), such as by being moved over a patient's body (or part thereof). For example, where the medical imaging system 110 is an ultrasound system, the probe 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost (by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110.

In some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other Cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In various implementations, the medical imaging system 110 may be configured to support real-time feedback for cardiopulmonary resuscitation (CPR) compressions, as described below.

FIG. 2 is a block diagram illustrating an example ultrasound system that supports ultrasound imaging with real-time feedback for cardiopulmonary resuscitation (CPR) compressions, in accordance with the present disclosure. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1 in ultrasound imaging use scenarios.

The ultrasound system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270. The user input device 230 may include button(s), rotary encoder(s), a touchscreen, motion tracking, voice recognition, a mouse device, keyboard, camera and/or any other device capable of receiving a user directive.

In certain embodiments, one or more of the user input devices 230 may be integrated into other components, such as the display system 260 or the ultrasound probe 204, for example. As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. Additionally and/or alternatively, the user input device 230 may include image analysis processing to identify probe gestures by analyzing acquired image data.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data may be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that may be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise a cardiopulmonary resuscitation (CPR) feedback module 242, which comprises suitable circuitry, interfaces, logic, and/or code that may be configured to perform and/or support various functions relating to providing and/or facilitating ultrasound imaging with real-time feedback for cardiopulmonary resuscitation (CPR).

In some implementations, the signal processor 240 (and/or components thereof, such as the CPR feedback module 242) may be configured to implement and/or use deep learning techniques and/or algorithms, such as using deep neural networks (e.g., a convolutional neural network), and/or may utilize any suitable form of artificial intelligence image analysis techniques or machine learning processing functionality configured to, e.g., analyze acquired ultrasound images, such as to identify, segment, label, and track structures meeting particular criteria and/or having particular characteristics. The CPR feedback module 242 may be configured for utilizing these techniques and/or capabilities in facilitating or supporting real-time feedback for cardiopulmonary resuscitation (CPR) compressions. For example, the CPR feedback module 242 may be configured to identify structures pertinent to evaluation CPR compressions, such as the aorta, the aortic outlet, the left ventricular (LV), the left ventricular outflow tract (LVOT), etc.

In an example implementation, the signal processor 240 (and/or components thereof, such as the CPR feedback module 242) may be provided as a deep neural network that may be made up of, for example, an input layer, an output layer, and one or more hidden layers in between the input and output layers. Each of the layers may be made up of a plurality of processing nodes that may be referred to as neurons.

For example, the deep neural network may include an input layer having a neuron for each pixel or a group of pixels from a scan plane of an anatomical structure. The output layer may have a neuron corresponding to a plurality of pre-defined structures or types of structures. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the deep neural network (e.g., convolutional neural network) may identify biological and/or artificial structures in ultrasound image data with a high degree of probability.

In certain implementations, the signal processor 240 (and/or components thereof, such as the CPR feedback module 242) may be configured to perform or otherwise control at least some of the functions performed thereby based on a user instruction via the user input device 230. As an example, a user may provide a voice command, probe gesture, button depression, or the like to issue a particular instruction, such as to provide real-time feedback during CPR operations, as described below.

The training engine 280 may comprise suitable circuitry, interfaces, logic, and/or code that may be operable to train the neurons of the deep neural network(s) of the signal processor 240 (and/or components thereof, such as the CPR feedback module 242). For example, the signal processor 240 (and/or components thereof, such as the CPR feedback module 242) may be trained to identify particular structures or types of structures provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images of particular structures to train the signal processor 240 (and/or components thereof, such as the CPR feedback module 242) with respect to the characteristics of the particular structure(s), such as the appearance of structure edges, the appearance of structure shapes based on the edges, the positions of the shapes relative to landmarks in the ultrasound image data, and the like. In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that may be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope may undergo additional B-mode processing, such as logarithmic compression to form the display data. The display data may be converted to X-Y format for video display. The scan-converted frames may be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception. For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations in accordance with the present disclosure, the ultrasound system 200 may be configured to support ultrasound imaging with real-time feedback for cardiopulmonary resuscitation (CPR) compressions. In this regard, in some instances, ultrasound systems such as the ultrasound system 200 may be configured for supporting ultrasound imaging in conjunction with cardiopulmonary resuscitation (CPR). For example, the ultrasound system 200 may be configured to generate and display ultrasound images while performing cardiopulmonary resuscitation (CPR) on a patient. To facilitate such use, the ultrasound system 200 may be adaptively designed and/or configured. For example, the probe 204 may be configured as transesophageal echocardiogram (TEE) probe or transthoracic echocardiogram (TTE) probe, which may allow transmitting and receiving ultrasound images in manner compatible with performing CPR and without interfering with these operations—e.g., in the parasternal view, which don't interfere with the compressions. Further, the ultrasound system 200 may be designed and/or implemented to be lightweight and/or portable, such that it may be mobile (and as such may be easily moved to and used on location where CPR is being performed).

Further, the ultrasound system 200 may be configured to provide real-time feedback to the user relating to the CPR operations (e.g., the CPR compressions being applied to the patient). In this regard, the ultrasound system 200 may be configured to generate the feedback, which may entail determining any information pertaining to the generation of feedback, and to provide (e.g., via suitable output device) the feedback. The feedback may comprise, for example, real-time visual feedback. In this regard, the ultrasound system 200 may be configured to generate the visual feedback, and to display the visual feedback, as well to perform any pertinent operations (e.g., determining information relating to the feedback, formatting the feedback, incorporating the feedback, etc.). For example, visual feedback may be done by incorporating generated visual feedback into the ultrasound images as they are displayed.

The real-time feedback may comprise feedback relating to compressions applied by the user during CPR, such as positioning of the compression—e.g., whether or not the position or location where the compression are applied is (or not) the correct and/or optimal position. For example, the ultrasound system 200 may be configured to, while compressions are being applied, identify structures pertinent to CPR (e.g., the aorta, the aortic outlet, the left ventricular (LV), and the left ventricular outflow tract (LVOT), etc.), to continually determine location of each compression, to determine area where majority of the compressions is applied, and to compare that area with location(s) of identified structure(s). This area may be referred as the "maximal compression area." The ultrasound system 200 may be configured to use different criteria for determining what constitute "majority" of the compression. The ultrasound system 200 may determine that area based on, for example, where more than half of the compressions are applied. Alternatively, in some instances a particular threshold (e.g., preset minimal percent of total compressions) may be used in assessing when a "majority" of compressions are applied in particular area.

Once determined, the maximal compression area may then be assessed to determine if the majority of compressions are applied correctly. In this regard, ideally CPR compressions should be above the left ventricle, and as such if CPR compressions may be assessed as being applied correctly if the maximal compression area corresponds to that location. The ultrasound system 200 may generate and provide CPR positioning feedback (e.g., visual feedback) based on such assessment.

For example, if the compressions are applied in a correct location, the ultrasound system 200 may provide a visual feedback indicating that (e.g., a green indicator over that area); if the compressions are applied in an incorrect location, the ultrasound system 200 may provide a different visual feedback indicating the incorrect location of compression (e.g., a red indicator over that area). In some instances, addition visual feedback may be provided. For example, where the maximal compression area corresponds to incorrect location, in addition to providing the incorrect location indication, the ultrasound system 200 may also provide additional visual feedback to assist the user in correcting the location (e.g., an arrow pointing to the direction that the user should reposition the hands for continuing compressions, for example, showing that the compressions be moved in the medial or lateral direction).

In some instances, the ultrasound system 200 may be configured to provide other types of feedback, beyond and/or in addition to location-related feedback. For example, the ultrasound system 200 may be configured to determine and provide feedback (e.g., visual feedback) relating to information pertinent to CPR operation. The ultrasound system 200 may be configured to, for example, track and/or determine CRP compression rate, and to generate and provide feedback (e.g., visual feedback) relating thereto.

For example, the ultrasound system 200 may be configured to calculate the volume flow rate, and to generate and display the waveform of the calculated carotid blood flow. In this regard, during CPR the user could use the patch probe for monitoring the carotid blood flow which indicates if an adequate amount of blood flows to the brain with each compression. The ultrasound system 200 may display the waveform, and according to the calculated flow rate, may provide a corresponding visual feedback (e.g., red indicator), indicating that the compression position is incorrect. The waveform peaks may be used to calculate the compressions rate, and the number may be shown, either by itself alone or in conjunction with the recommended rate of compressions in CPR (e.g., 100-120 compressions per minute). In this regard, the feedback may be visually altered to indicate whether the compression rate is correct or not. For example, if the actual compression rate is lower than minimal recommended rate (e.g., 100 compressions per minute), the compression rate may be marked particular manner (e.g., in red).

In some instances, the ultrasound system 200 may be configured to provide non-visual feedback, such as audible. For example, the ultrasound system 200 may be configured to generate and output a warning audible beep to indicate any issues with the CPR operations as being performed—e.g., incorrect position/location, incorrect compression rate, etc. This may be done with or without providing visual feedback too.

In some instances, the ultrasound system 200 may be configured to store data relating to CPR operations, to enable improving the accuracy and effectiveness of CPR operations. For example, the ultrasound system 200 may be configured to store and retrieve images that correspond to specific body zone of the patients on whom CPR is performed.

Consequently, implementations in accordance with the present disclosure may enhance cardiopulmonary resuscitation (CPR) operations by providing users (e.g., physicians, clinicians) real-time feedback about the effectiveness of the CPR (e.g., the CPR compressions being applied), to warn the users when something is not being done correctly and/or optimally (e.g., location of compressions), and to indicate how to make corrections (e.g., how to correct the location and/or position of the hands), thus allowing for immediately improving the quality of the compressions which are the main factor for success of CPR.

Figure 3:
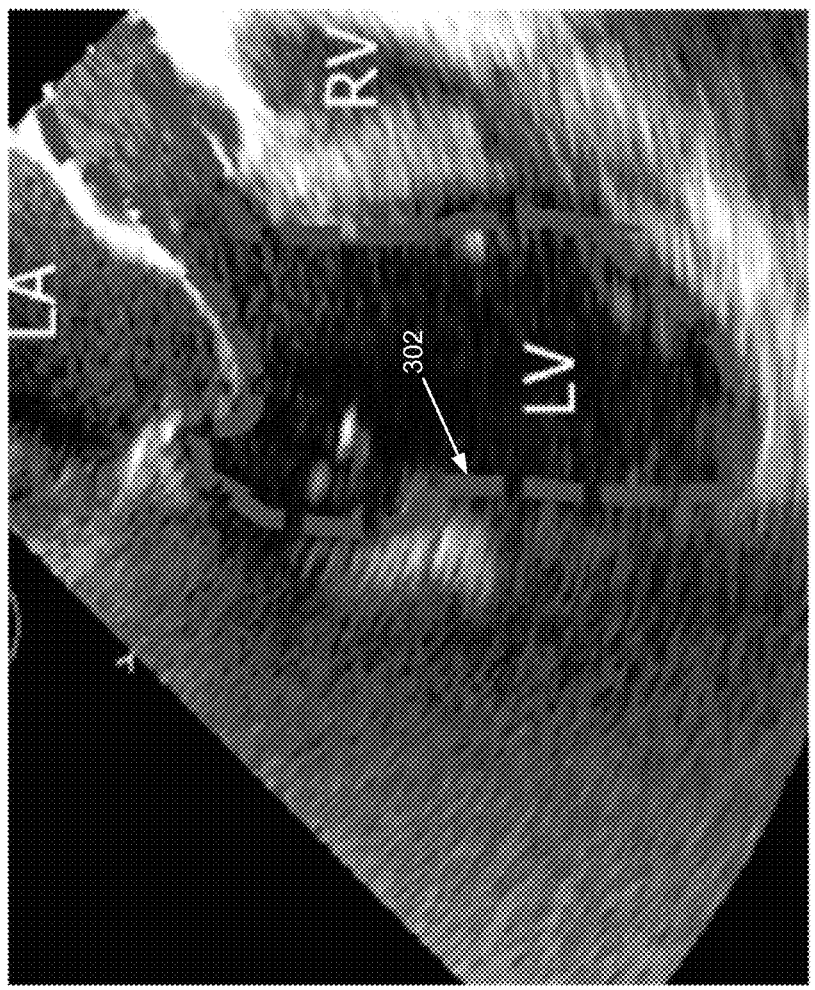
FIG. 3 illustrates an example ultrasound image showing the heart and surrounding area, which may be generated via an ultrasound system configured for supporting cardiopulmonary resuscitation (CPR) operations in accordance with the present disclosure.

FIG. 3 illustrates an example ultrasound image showing the heart and surrounding area, which may be generated via an ultrasound system configured for supporting cardiopulmonary resuscitation (CPR) operations in accordance with the present disclosure. Shown in FIG. 3 is a screenshot of an ultrasound image 300.

The ultrasound image 300 may represent an ultrasound image of a heart and surrounding area generated when performing ultrasound imaging during cardiopulmonary resuscitation (CPR), in a system implemented in accordance with the present disclosure, such as the ultrasound system 200 of FIG. 2. In particular, the ultrasound image 300 may represent an ultrasound image of a heart and surrounding area. In this regard, the ultrasound image 300 may be generated when performing ultrasound imaging during cardiopulmonary resuscitation (CPR). Thus, such ultrasound images may include such structures and/or areas as the heart champers (of which the left ventricle (LV), right ventricle (RV), and left atrium (LA) are shown in FIG. 3).

In accordance with the present disclosure, ultrasound images generated during cardiopulmonary resuscitation (CPR) may be processed to support providing real-time feedback relating to the CPR. For example, the ultrasound images (or datasets corresponding thereto) may be processed to such that the images (or areas included therein) may be automatically segmented. The segmenting may be directed to particular structures and/or areas that are pertinent to CPR compressions.

For example, segmenting the ultrasound image frames, and the segments may be matched to corresponding structures or areas, to enable identifying segments that match structures/areas pertinent to CPR—e.g., the left ventricle (LV) 302. The location of each compression may be tracked, and matched to the corresponding segment. The segment that is most compressed over time may then be calculated or determined, as explained above.

The most compressed segment may then be assessed for determining whether (or not) it correspond to a correction position for applying CPR compressions, such as by determining if the most contracted segment is part of the LV 302 (or other pertinent parts/structures, such as the of the aorta, etc.). That determination may be used in generating and/or configuring feedback (e.g., visual feedback), as illustrated in FIG. 4.

Figure 4:
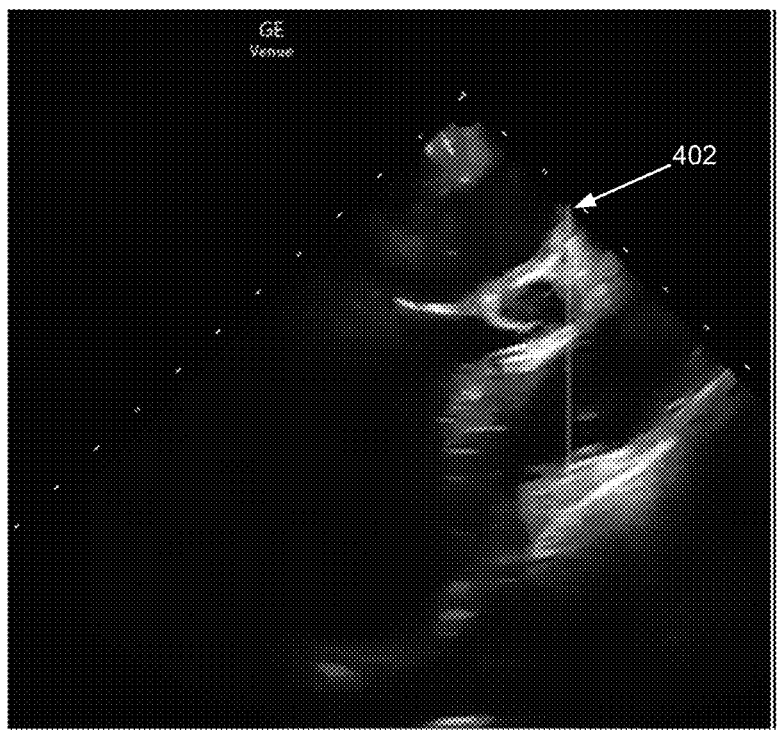
FIG. 4 illustrates example ultrasound images that incorporate real-time visual feedback relating to location of cardiopulmonary resuscitation (CPR) compressions, in accordance with the present disclosure.
Figure 4:
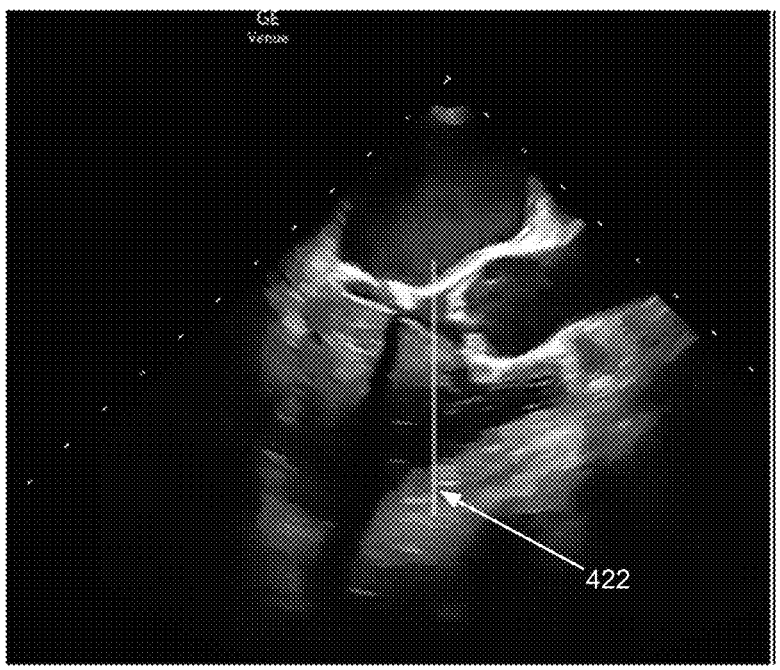

FIG. 4 illustrates example ultrasound images that incorporate real-time visual feedback relating to location of cardiopulmonary resuscitation (CPR) compressions, in accordance with the present disclosure. Shown in FIG. 4 are screenshots of ultrasound images 400 and 420.

The ultrasound images 400 and 420 may represent ultrasound images of a heart and surrounding area that are generated when performing ultrasound imaging during cardiopulmonary resuscitation (CPR), in a system implemented in accordance with the present disclosure, such as the ultrasound system 200 of FIG. 2. In particular, the ultrasound images 400 and 420 illustrated example real-time visual feedback that may be provided during example use scenario of the ultrasound image 200 when used in conjunction with conduction CPR on a patient.

As explained above, the locations of compressions may be monitored and/or determined—e.g., based on processing of ultrasound images (or datasets corresponding thereto), and correspondingly, the maximal compression area may be determined. The maximal compression area (or location thereof) may then be compared with the location determined as being the "correct" location for applying CPR compressions. In this regard, the correct location may correspond to particular pertinent structures, such as the LV. A visual feedback may then be generated and/or configured based on the outcome of the comparison, and applied into displayed ultrasound images.

For example, as shown in the example implementation shown in FIG. 4, the visual feedback may be a visual indicator (e.g., line) over the maximal compression area, and having different characteristics based on the outcome of the assessment of the maximal compression area. Thus, if the maximal compression area corresponds to incorrect position (e.g., over the aortic outlet, as shown in image 400, or over the left ventricular outflow tract (LVOT)), a visual indictor 402 indicating an incorrect position may be generated and configured in particular manner (e.g., as red line) to indicate to the user that the compressions are generally applied in the wrong position. If the maximal compression area corresponds to correct position (e.g., over the left ventricle, as shown in image 420), a visual indictor 422 indicating a correct position may be generated and configured in particular manner (e.g., as green line) to indicate to the user that the compressions are generally applied in the correct position.

In some instances, additional visual feedback may be generated and provided. For example, while not shown in FIG. 4, in addition to including the visual indicator 402 (for indicating incorrect position), a visual feedback may additionally be incorporated in ultrasound image 402 to help aid the user in applying the compressions the correct position—e.g., an arrow may be generated and display showing the user how to correct the hands' position (e.g., pointing to the area corresponding to the LV).

Figure 5:
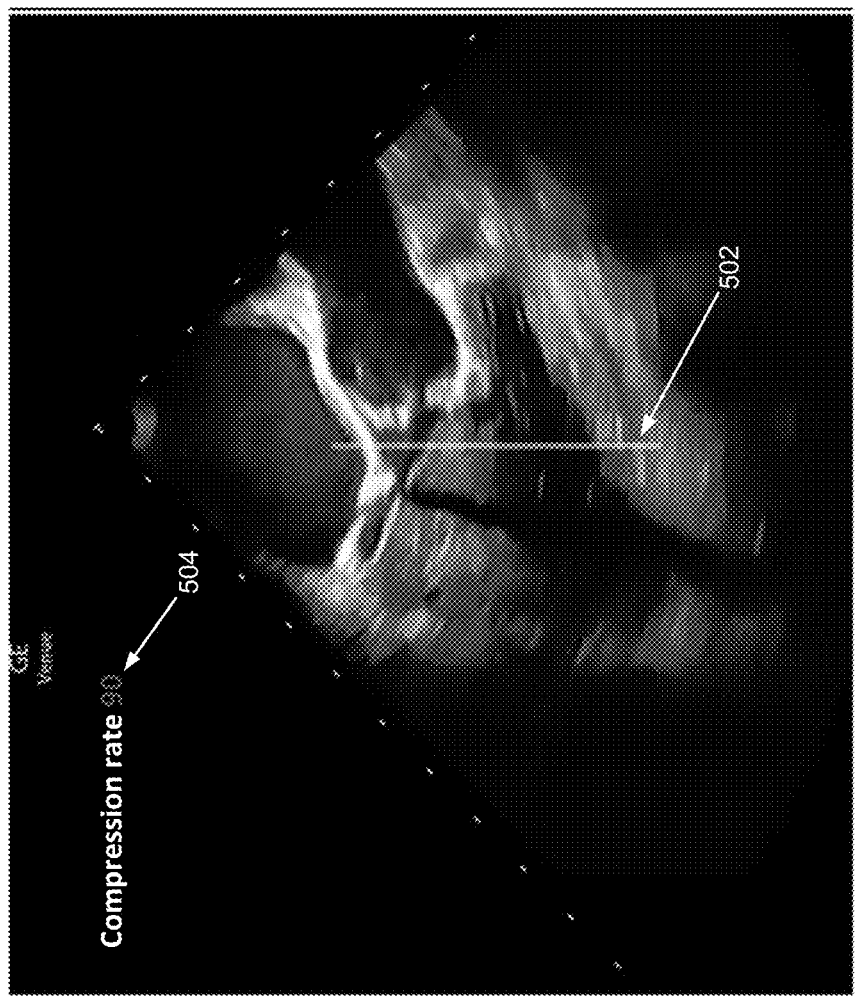
FIG. 5 illustrates example ultrasound image that incorporates real-time visual feedback relating to location of and additional data pertaining to cardiopulmonary resuscitation (CPR) compressions, in accordance with the present disclosure.

FIG. 5 illustrates example ultrasound images that incorporate real-time visual feedback relating to location of cardiopulmonary resuscitation (CPR) compressions, in accordance with the present disclosure. Shown in FIG. 5 are screenshots of ultrasound image 500.

The ultrasound image 500 may represent an example ultrasound image of a heart and surrounding area generated when performing ultrasound imaging during cardiopulmonary resuscitation (CPR), in a system implemented in accordance with the present disclosure, such as the ultrasound system 200 of FIG. 2. In particular, the ultrasound image 500 illustrates example real-time visual feedback that may be provided during example use scenario of the ultrasound image 200 when used in conjunction with conduction CPR on a patient.

Specifically, the ultrasound image 500 shows use of additional visual feedback beyond location-related visual feedback. For example, as shown in FIG. 5, the ultrasound image 500 incorporates a location visual indicator 502, which (as shown in FIG. 5) indicates a correct position for the majority of applied compressions. In this regard, as described above, the location visual indicator may be generated and/or configured based on determination of the maximal compression area (e.g., by tracking location of each compression over time), and assessment thereof (e.g., based on comparison of the location of the maximal compression area with the location of structures where compressions should be applied, such as the left ventricle (LV)).

However, the ultrasound image 500 includes additional visual feedback relating to the CPR operations. For example, as shown in FIG. 5, the ultrasound image 500 includes visual feedback relating to the compression rate. In this regard, the compression rate may be determined in various ways, such as based on flow calculation as explained above. For example, the compression rate may be calculated from waveform peaks of the carotid flow, as described above.

Once determined, the compression rate may be displayed on the ultrasound image. In this regard, the manner the compression rate is displayed (e.g., visually) may be changed based on pertinent criteria. Thus, where the compression rate as calculated (e.g., 90 as shown in FIG. 5) is determined to be below a particular value or range, which be predefined as recommended range (e.g., 100-120 compressions per minute), the calculated compression rate may be displayed in red. Conversely, when the calculated compression rate is within the recommended range, it may be displayed in green.

Figure 6:
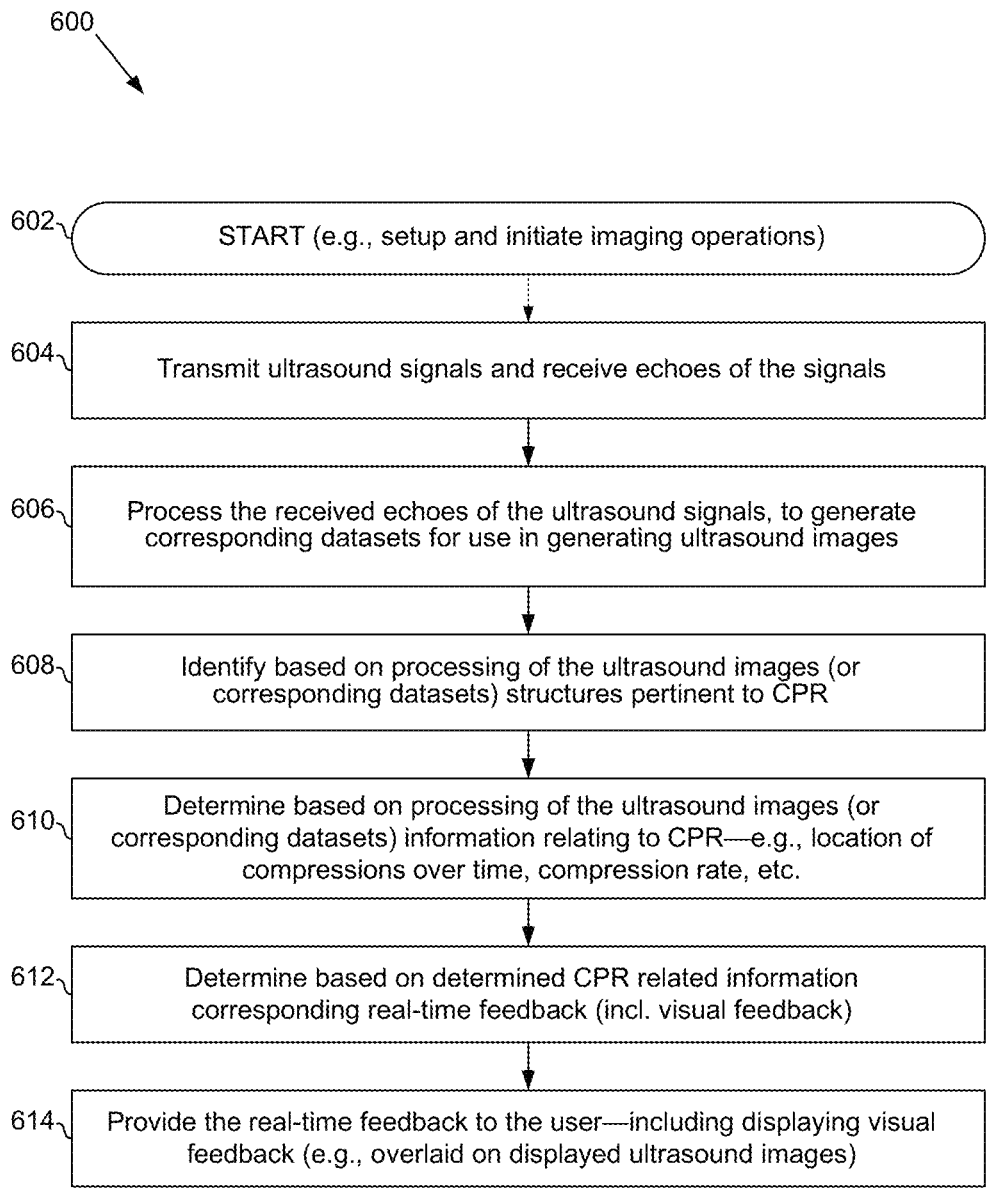
FIG. 6 illustrates a flowchart of an example steps that may be performed for ultrasound imaging with ultrasound imaging with real-time feedback for cardiopulmonary resuscitation (CPR) compressions.

FIG. 6 illustrates a flowchart of an example steps that may be performed for ultrasound imaging with ultrasound imaging with real-time feedback for cardiopulmonary resuscitation (CPR) compressions.

Shown in FIG. 6 is flow chart 600, comprising a plurality of example steps (represented as blocks 602-614), which may be performed in a suitable system (e.g., system 200 of FIG. 2) for ultrasound imaging with real-time feedback for cardiopulmonary resuscitation (CPR).

In start step 602, the system may be setup, and operations may initiate.

In step 604, ultrasound signals may be transmitted, and corresponding echoes of the signals may be received.

In step 606, the received echoes of the ultrasound signals may be processed, to generate corresponding datasets for use in generating ultrasound images.

In step 608, based on processing of the ultrasound images (or corresponding datasets), structures pertinent to CPR may be identified.

In step 610, based on processing of the ultrasound images (or corresponding datasets), information relating to CPR—e.g., location of compressions over time, compression rate, etc.

In step 612, corresponding real-time feedback (incl. visual feedback) may be determined based on determined CPR related information corresponding real-time feedback (incl. visual feedback).

In step 614, the real-time feedback may be provided to the user, including displaying visual feedback (e.g., overlaid on displayed ultrasound images).

An example ultrasound system, in accordance with the present disclosure, for use in support of cardiopulmonary resuscitation (CPR) operations comprises an ultrasound probe configured to transmit ultrasound signals and receive echo ultrasound signals; a display configured to display ultrasound images; and one or more circuits configured to process ultrasound images generated based on received echo ultrasound signals during cardiopulmonary resuscitation (CPR) of a patient; determine based on the processing of the ultrasound images, real-time information relating to the cardiopulmonary resuscitation (CPR); generate based on the information, feedback for assisting in conducting the cardiopulmonary resuscitation (CPR). The feedback comprises information and/or indications relating to compressions applied during the cardiopulmonary resuscitation (CPR); is configured for output during displaying of the generated ultrasound images.

In an example implementation, the one or more circuits are configured to segment each ultrasound image into a plurality of segments; determine in which segment of the plurality of segments a location where each compression is applied; and continuously identify which segment of the plurality of segment is where a majority of compressions are applied over time.

In an example implementation, the one or more circuits are configured to determine a maximal compression area, wherein the maximal compression area corresponds to a location where a majority of compressions are applied; and assess based on one or more criteria associated with cardiopulmonary resuscitation (CPR), whether the maximal compression area corresponds to a correct position or an incorrect position.

In an example implementation, the one or more circuits are configured to generate different indicators based on determination that the maximal compression area corresponds to the correct position or the incorrect position.

In an example implementation, the one or more circuits are configured to generate indication for adjusting location where compressions are applied to match the correct position.

In an example implementation, the one or more circuits are configured to determine based on the processing of the ultrasound images, location of one or more structures pertinent to the cardiopulmonary resuscitation (CPR); and compare location where each compression is applied with location of each of the one or more structures. The one or more structures may comprise aorta, aortic outlet, left ventricular (LV), and left ventricular outflow tract (LVOT)

An example method, in accordance with the present disclosure, for supporting cardiopulmonary resuscitation (CPR) operations comprises processing ultrasound images generated based on received echo ultrasound signals during cardiopulmonary resuscitation (CPR) of a patient; determining based on the processing of the ultrasound images, real-time information relating to the cardiopulmonary resuscitation (CPR); generating based on the information, feedback for assisting in conducting the cardiopulmonary resuscitation (CPR). The feedback comprises information and/or indications relating to compressions applied during the cardiopulmonary resuscitation (CPR); and is configured for outputting during displaying of the generated ultrasound images.

In an example implementation, the method further comprises segmenting each ultrasound image into a plurality of segments; determining in which segment of the plurality of segments a location where each compression is applied; and continuously identifying which segment of the plurality of segment is where a majority of compressions are applied over time.

In an example implementation, the method further comprises determining a maximal compression area, wherein the maximal compression area corresponds to a location where a majority of compressions are applied; and assessing based on one or more criteria associated with cardiopulmonary resuscitation (CPR), whether the maximal compression area corresponds to a correct position or an incorrect position.

In an example implementation, the method further comprises generating different indicators based on determination that the maximal compression area corresponds to the correct position or the incorrect position.

In an example implementation, the method further comprises generating an indication for adjusting location where compressions are applied to match the correct position.

In an example implementation, the method further comprises determining based on the processing of the ultrasound images, location of one or more structures pertinent to the cardiopulmonary resuscitation (CPR); and comparing location where each compression is applied with location of each of the one or more structures. The one or more structures may comprise aorta, aortic outlet, left ventricular (LV), and left ventricular outflow tract (LVOT).

An example non-transitory computer readable medium, in accordance with the present disclosure, may have stored thereon a computer program having at least one code section, the at least one code section being executable in an ultrasound device for causing the ultrasound device to support of cardiopulmonary resuscitation (CPR) operations, by performing one or more steps that comprise processing ultrasound images generated based on received echo ultrasound signals during cardiopulmonary resuscitation (CPR) of a patient; determining based on the processing of the ultrasound images, real-time information relating to the cardiopulmonary resuscitation (CPR); and generating based on the information, feedback for assisting in conducting the cardiopulmonary resuscitation (CPR). The feedback comprises information and/or indications relating to compressions applied during the cardiopulmonary resuscitation (CPR); and is configured for outputting during displaying of the generated ultrasound images.

In an example implementation, the one or more steps further comprise segmenting each ultrasound image into a plurality of segments; determining in which segment of the plurality of segments a location where each compression is applied; and continuously identifying which segment of the plurality of segment is where a majority of compressions are applied over time.

In an example implementation, the one or more steps further comprise determining a maximal compression area, wherein the maximal compression area corresponds to a location where majority of compressions are applied; and assessing based on one or more criteria associated with cardiopulmonary resuscitation (CPR), whether the maximal compression area corresponds to a correct position or an incorrect position.

In an example implementation, the one or more steps further comprise generating different indicators based on determination that the maximal compression area corresponds to the correct position or the incorrect position.

In an example implementation, the one or more steps further comprise generating an indication for adjusting location where compressions are applied to match the correct position.

In an example implementation, processing the ultrasound images further comprises determining based on the processing of the ultrasound images, location of one or more structures pertinent to the cardiopulmonary resuscitation (CPR); and comparing location where each compression is applied with location of each of the one or more structures.

The may comprise aorta, aortic outlet, left ventricular (LV), and left ventricular outflow tract (LVOT).

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. An ultrasound system for use in support of cardiopulmonary resuscitation (CPR) operations, the system comprising:
    an ultrasound probe configured to transmit ultrasound signals and receive echo ultrasound signals;
    a display configured to display ultrasound images; and
    one or more circuits configured to:
        process ultrasound images generated based on received echo ultrasound signals during cardiopulmonary resuscitation (CPR) of a patient;
        identify based on the processing of the ultrasound images, at least one anatomical structure pertinent to the cardiopulmonary resuscitation (CPR), the at least one anatomical structure being an anatomical structure associated with the heart;
        determine based on the processing of the ultrasound images, real-time information relating to the cardiopulmonary resuscitation (CPR); and
        generate based on the information, feedback for assisting in conducting the cardiopulmonary resuscitation (CPR);
    wherein:
        the feedback comprises information and/or indications relating to compressions applied during the cardiopulmonary resuscitation (CPR);
        the feedback is configured for output during displaying of the generated ultrasound images; and
        the feedback comprises at least one visual indication, associated with applying the compressions, relative to the at least one anatomical structure in the generated ultrasound images.

2. The ultrasound system of claim 1, wherein the one or more circuits are configured to:
    segment each ultrasound image into a plurality of segments;
    determine in which segment of the plurality of segments a location where each compression is applied; and
    continuously identify which segment of the plurality of segment is where a majority of compressions are applied over time.

3. The ultrasound system of claim 1, wherein the one or more circuits are configured to:
    determine a maximal compression area, wherein the maximal compression area corresponds to a location where a majority of compressions are applied; and
    assess based on one or more criteria associated with cardiopulmonary resuscitation (CPR), whether the maximal compression area corresponds to a correct position or an incorrect position.

4. The ultrasound system of claim 3, wherein the one or more circuits are configured to generate different indicators based on determination that the maximal compression area corresponds to the correct position or the incorrect position.

5. The ultrasound system of claim 4, wherein the one or more circuits are configured to generate indication for adjusting location where compressions are applied to match the correct position.

6. The ultrasound system of claim 1, wherein the one or more circuits are configured to:
determine based on the processing of the ultrasound images, location of the at least one anatomical structure; and
compare location where each compression is applied with location of the at least one anatomical structure.

7. A method for supporting cardiopulmonary resuscitation (CPR) operations, the method comprising:
acquiring, via an ultrasound probe of a medical imaging system, during cardiopulmonary resuscitation (CPR) of a patient, echo ultrasound signals corresponding to ultrasound signals transmitted via by ultrasound probe;
processing, by at least one processor of the medical imaging system, ultrasound images generated based on the received echo ultrasound signals;
identifying, by the at least one processor, based on the processing of the ultrasound images, at least one anatomical structure pertinent to the cardiopulmonary resuscitation (CPR), the at least one anatomical structure being an anatomical structure associated with the heart;
determining, by the at least one processor, based on the processing of the ultrasound images, real-time information relating to the cardiopulmonary resuscitation (CPR); and
generating, by the at least one processor, based on the information, feedback for assisting in conducting the cardiopulmonary resuscitation (CPR);
wherein:
the feedback comprises information and/or indications relating to compressions applied during the cardiopulmonary resuscitation (CPR);
the feedback is configured for outputting during displaying of the generated ultrasound images; and
the feedback comprises at least one visual indication, associated with applying the compressions, relative to the at least one anatomical structure in the generated ultrasound images.

8. The method of claim 7, further comprising:
segmenting each ultrasound image into a plurality of segments;
determining in which segment of the plurality of segments a location where each compression is applied; and
continuously identifying which segment of the plurality of segment is where a majority of compressions are applied over time.

9. The method of claim 7, further comprising:
determining a maximal compression area, wherein the maximal compression area corresponds to a location where a majority of compressions are applied; and
assessing based on one or more criteria associated with cardiopulmonary resuscitation (CPR), whether the maximal compression area corresponds to a correct position or an incorrect position.

10. The method of claim 9, comprising generating different indicators based on determination that the maximal compression area corresponds to the correct position or the incorrect position.

11. The method of claim 10, comprising generating an indication for adjusting location where compressions are applied to match the correct position.

12. The method of claim 7, further comprising:
determining based on the processing of the ultrasound images, location of the at least one anatomical structure; and
comparing location where each compression is applied with location of the at least one anatomical structure.

13. The method of claim 12, wherein the at least one anatomical structure comprises aorta, aortic outlet, left ventricular (LV), or left ventricular outflow tract (LVOT).

14. A non-transitory computer readable medium having stored thereon, a computer program having at least one code section, the at least one code section being executable in an ultrasound device for causing the ultrasound device to for causing the ultrasound device to support of cardiopulmonary resuscitation (CPR) operations, by performing one or more steps comprising:
processing ultrasound images generated based on received echo ultrasound signals during cardiopulmonary resuscitation (CPR) of a patient;
identifying based on the processing of the ultrasound images, at least one anatomical structure pertinent to the cardiopulmonary resuscitation (CPR), the at least one anatomical structure being an anatomical structure associated with the heart;
determining based on the processing of the ultrasound images, real-time information relating to the cardiopulmonary resuscitation (CPR); and
generating based on the information, feedback for assisting in conducting the cardiopulmonary resuscitation (CPR);
wherein:
the feedback comprises information and/or indications relating to compressions applied during the cardiopulmonary resuscitation (CPR);
the feedback is configured for outputting during displaying of the generated ultrasound images; and
the feedback comprises at least one visual indication, associated with applying the compressions, relative to the at least one anatomical structure in the generated ultrasound images.

15. The non-transitory computer readable medium of claim 14, the one or more steps further comprising:
segmenting each ultrasound image into a plurality of segments;
determining in which segment of the plurality of segments a location where each compression is applied; and
continuously identifying which segment of the plurality of segment is where a majority of compressions are applied over time.

16. The non-transitory computer readable medium of claim 14, the one or more steps further comprising:
determining a maximal compression area, wherein the maximal compression area corresponds to a location where majority of compressions are applied; and
assessing based on one or more criteria associated with cardiopulmonary resuscitation (CPR), whether the maximal compression area corresponds to a correct position or an incorrect position.

17. The non-transitory computer readable medium of claim 16, the one or more steps further comprising generating different indicators based on determination that the maximal compression area corresponds to the correct position or the incorrect position.

18. The non-transitory computer readable medium of claim 17, the one or more steps further comprising generating an indication for adjusting location where compressions are applied to match the correct position.

19. The non-transitory computer readable medium of claim 14, wherein processing the ultrasound images comprises:
- determining based on the processing of the ultrasound images, location of the at least one anatomical structure; and
- comparing location where each compression is applied with location of the at least one anatomical structure.

20. The non-transitory computer readable medium of claim 19, wherein the at least one anatomical structure comprises aorta, aortic outlet, left ventricular (LV), or left ventricular outflow tract (LVOT).

* * * * *